United States Patent [19]

Shiokawa et al.

[11] Patent Number: 4,619,688
[45] Date of Patent: Oct. 28, 1986

[54] HERBICIDAL SULFONYLGUANIDINE DERIVATIVES

[75] Inventors: Kozo Shiokawa, Kawasaki; Koichi Moriya, Hachioji; Toshio Goto, Sagamihara; Atsumi Kamochi, Hino; Shigeo Kohama, Hachioji, all of Japan

[73] Assignee: Nihon Tokushu Noyaku Seizo K.K., Tokyo, Japan

[21] Appl. No.: 688,844

[22] Filed: Jan. 4, 1985

[30] Foreign Application Priority Data

Jan. 10, 1984 [JP] Japan .................................. 59-1257

[51] Int. Cl.⁴ ................. C07D 239/34; C07D 239/42; C07D 413/12; A01N 43/54
[52] U.S. Cl. ........................ 71/92; 544/321; 544/332; 544/122; 544/123
[58] Field of Search ............... 544/321, 332, 122, 123; 71/92

[56] References Cited

U.S. PATENT DOCUMENTS 4,310,346 1/1982 Levitt et al. .................. 544/211
4,484,939 11/1984 Tseng ...................... 71/92

FOREIGN PATENT DOCUMENTS 0023141 1/1981 European Pat. Off. .
0043642 1/1982 European Pat. Off. .

Primary Examiner—John M. Ford

Attorney, Agent, or Firm—Sprung Horn Kramer & Woods

[57] ABSTRACT

Selectively herbicidal compounds of the formula

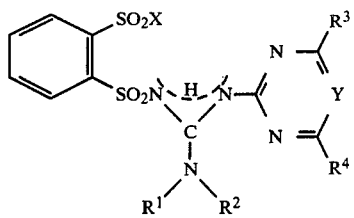

in which
$R^1$ is a hydrogen atom or the group

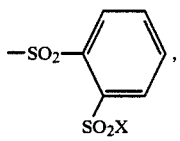

$R^2$ is a hydroxy group, a lower alkoxy group or a di-lower alkylamino group,
$R^3$ and $R^4$ each independently is a lower alkyl group or a lower alkoxy group,
X is a lower alkoxy group, a lower alkylamino group or a morpholino group, and
Y is N or CH.

9 Claims, No Drawings

HERBICIDAL SULFONYLGUANIDINE DERIVATIVES

DETAILED DESCRIPTION OF THE INVENTION

This invention relates to novel sulfonylguanidine derivatives, processes for production thereof and a herbicide.

More specifically, this invention relates to sulfonylguanidine derivatives represented by the following formula (I).

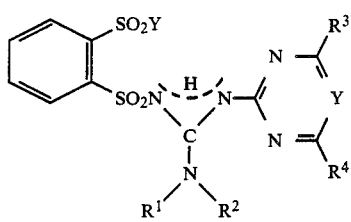

in which
R$^1$ is a hydrogen atom or the group

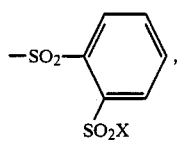

R$^2$ is a hydroxy group, a lower alkoxy group or a di-lower alkylamino group,
R$^3$ and R$^4$ each independently is a lower alkyl group or a lower alkoxy group,
X is a lower alkoxy group, a lower alkylamino group or a morpholino group, and
Y is N or CH.

The compounds of general formula (I) of this invention can be produced by the following processes to which the invention also pertains.

PROCESS (i)

A process for producing the sulfonylguanidine of general formula (I) above, which comprises reacting a compound represented by the formula

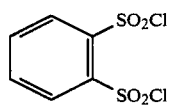

with a compound represented by the general formula

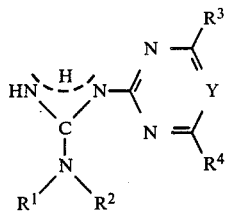

wherein R$^1$, R$^2$, R$^3$, R$^4$ and Y are as defined above, with a compound represented by the general formula

M—X    (IV)

wherein X is as defined above, and M represents a hydrogen atom or an alkali metal atom.

PROCESS (ii)

A process for producing the sulfonylguanidine derivative of general formula (I), which comprises reacting a compound represented by the general formula

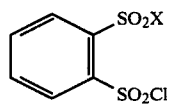

wherein X is as defined above,
with compound of general formula (III) given above in the presence of a base.

PROCESS (iii)

A process for producing the sulfonylguanidine of general formula (I), which comprises reacting a compound represented by the general formula

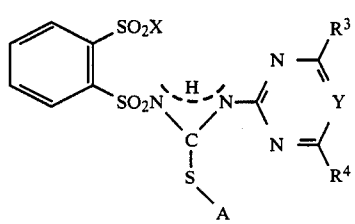

wherein X, R$^3$, R$^4$, Y and M are as defined above, and A represents a lower alkyl group, with a compound represented by the general formula

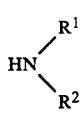

wherein R$^1$ and R$^2$ are as defined above.

The invention also relates to a herbicide comprising the sulfonylguanidine derivative of general formula (I) as an active ingredient.

The compounds of this invention are characterized by the fact that biologically, they have excellent selective herbicidal activity especially against upland farm weeds without causing phytotoxicity to upland farm crops such as soybean, and winter wheat. They have low toxicity to warm-blooded animals and are not phytotoxic to cultivated crops when applied in the usual dosages. They exhibit an outstanding selective control efficacy when used as a pre-emergence soil treating agent and a stalk-foliar/soil treating agent against a broad range of weeds grown in upland farms. pre-emergence soil treating agent and a stalk-foliar/soil treating agent against a broad range of weeds grown in upland farms.

They are herbicidal to *Alopecurus aequalis* Sobol. var. *amurensis* Ohwi, *Setaria glauca* P. Beauv., *Stellaria media* Villars, *Echinochloa crus-galli* P. Beauv., *Digitaria adscendens* Henr., *Eleusine indica* Gaertn., *Digitaria violascens* Link, *Amaranthus lividus* Loisel., *Polygonum* blumei Meisn., *Chenopodium album* L., *Chenopodium ficifolium* Smith, *Amaranthus refroflexus* L., *Poa annua* L., *Rorippa palustris* Bess., *Polygonum nepalense* Meisn., *Rumex obtusifolius* L., *Rumex japonicus* Houtt., *Lamium amplexicauls* L., *Galium spurium* L., *Stellaria alsine* Grimn, *Cardamine flexuosa* With., and *Polygonum ariculars* L.

The compounds of this invention exhibit strong herbicidal activity on weeds other than those exemplified above. For example, it has been observed that they have an excellent herbicidal efficacy and a reproduction inhibiting effect against perennial weeds which are difficult to control, for example *Cyperus rotundus* L., and *Cynodon dactylon* Pers.

The compounds of this invention can be used safely without causing toxicity to many crops including beans, wheat, cotton, carrot, potato, beet, cabbage, mustard, peanut, radish, tobacco, tomato and cucumber.

The adaptability of the active compounds of this invention is not limited to upland farm weeds, and they are also effective against weeds noxious to rice and mat rush, and weeds in farms which are out of cultivation. The term "weeds", as used herein, mean all plants which grow in undesired loci in the broadest sense.

The compounds of general formula (I) of this invention can be produced by the following general Processes (i), (ii) and (iii).

PROCESS (i)

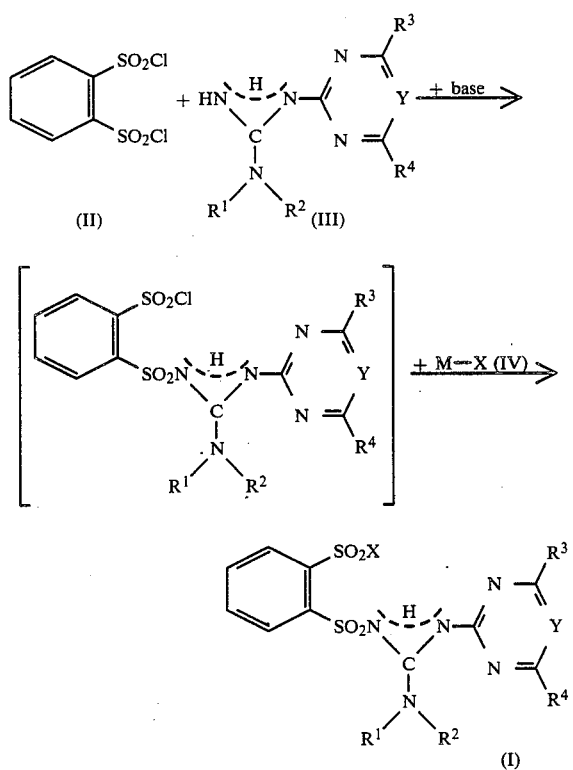

(In the formulae, $R^1$, $R^2$, $R^3$, $R^4$, Y, X and M are the same as defined hereinabove.)

In the above reaction scheme, X represents a lower alkoxy group, a lower alkylamino group or a morpholino group. Specific examples of the lower alkoxy groups are those containing lower alkyl groups such as methyl, ethyl, propyl, iropropyl and n-(iso-, sec-, or tert-)butyl. Specific examples of the lower alkylamino group may be those having the same lower alkyl groups as exemplified above.

$R^1$ represents a hydrogen atom, or the group of the formula

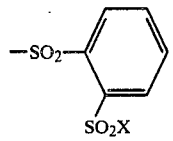

in which X is as defined above.

$R^2$ represents a hydroxy group, a lower alkoxy group, or a di-(lower alkyl)amino group. Examples of the lower alkoxy group are the same as given above. Examples of the di-(lower alkyl)amino group are amino groups di-substituted by the same lower alkyl groups as above. The lower alkyl groups may be identical or different.

Each of $R^3$ and $R^4$ represents a lower alkyl group or a lower alkoxy group. Examples of the lower alkyl group and the lower alkoxy group are the same as those given above.

Y represents N or CH.

M represents a hydrogen atom, or an alkali metal atom such as sodium, potassium and lithium.

Specific examples of the starting compound of general formula (III) in the above reaction scheme include N-(4,6-dimethylpyrimidin-2-yl) N'-methoxyguanidine,
N-(4,6-dimethoxy-1,3,5-triazin-2-yl) N'-methoxyguanidine,
N-(4-methoxy-6-methylpyrimidin-2-yl) N'-methoxyguanidine,
N-(4,6-dimethylpyrimidin-2-yl) N'-hydroxyguanidine,
N-(4,6-dimethylpyrimidin-2-yl) N'-(methoxy) N'-(2-ethoxysulfonylbenzenesulfonyl)guanidine, and
N-(4,6-dimethylpyrimidin-2-yl) N'-dimethylaminoguanidine.

Specific examples of the compound of general formula (IV) which is likewise a starting material include sodium methylate,
sodium ethylate,
ammonia,
methylamine, and
morpholine.

Pyridine is an example of the base used in the above reaction.

An illustrative example of Process (i) is as follows:

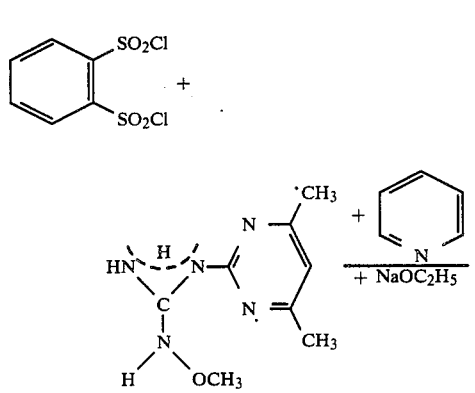

-continued

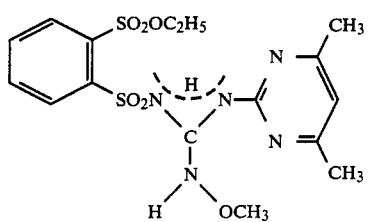

Desirably, the above process for producing the compound of this invention can be carried out using a solvent or a diluent. For this purpose, all inert solvents and diluents can be used.

Examples of such solvents or diluents include water; aliphatic, alicyclic and aromatic hydrocarbons (which may optionally be chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, diisopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; alcohols such as methanol, ethanol, isopropanol, butanol and ethylene glycol; esters such as ethyl acetate and amyl acetate; acid amides such as dimethylformamide and dimethylacetamide; sulfones and sulfoxides such as dimethyl sulfoxide and sulfolane; and bases such as pyridine.

The above reaction may be carried out in the presence of an acid binder. Examples of the acid binder include the hydroxides, carbonates, bicarbonates and alcoholates of alkali metals and tertiary amines such as triethylamine, diethylaniline and pyridine, all of which are generally used.

The process of this invention can be carried out over a wide temperature range. Generally, it can be carried out at a temperature between about −20° C. and the boiling point of the mixture, desirably between about 0° C. and about 100° C. Desirably, the reaction is carried out under normal atmospheric pressure, but it is also possible to operate under elevated or reduced pressures.

PROCESS (ii)

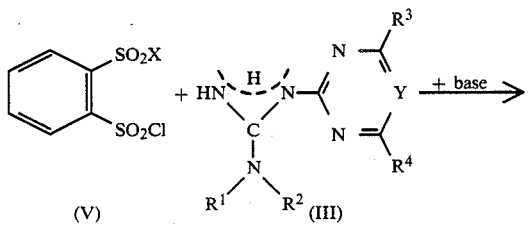

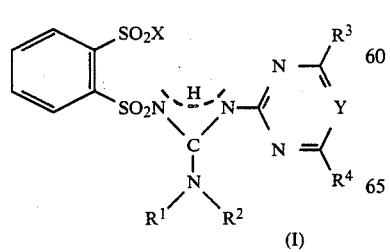

In the above formulae, $R^1$, $R^2$, $R^3$, $R^4$, Y and X are the same as defined above.

In the above reaction scheme, $R^1$, $R^2$, $R^3$, $R^4$, Y and X are the same as defined above with regard to Process (i).

Specific examples of the starting compound of general formula (V) include
2-methoxysulfonylbenzenesulfonyl chloride,
2-ethoxysulfonylbenzenesulfonyl chloride,
2-morpholinosulfonylbenzenesulfonyl chloride,
2-methylaminosulfonylbenzenesulfonyl chloride, and
2-aminosulfonylbenzenesulfonyl chloride.

Specific examples of the other starting compound of general formula (III) are the same as those given above with regard to Process (i).

A specific example of the base is the same as given above with regard to Process (i).

An illustrative example of Process (ii) is as follows:

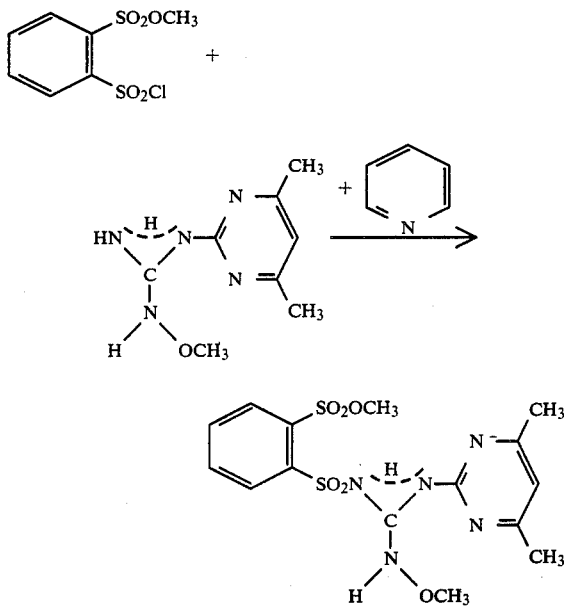

Desirably, the Process (ii) is carried out by using the same inert solvent or diluent as exemplified above, and the desired final product of high purity can be obtained in a high yield.

As is the case with Process (i), the Process (ii) can be carried out over a broad temperature range. Desirably, the reaction is carried out under normal atmospheric pressure, but it is also possible to operate under elevated or reduced pressures.

PROCESS (iii)

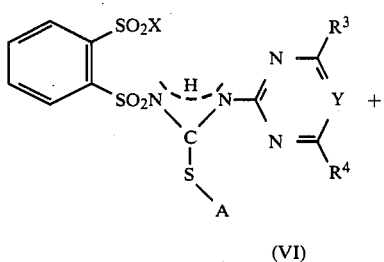

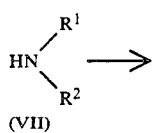

(VII)

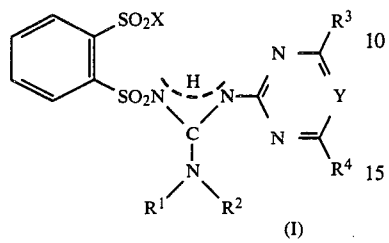

(I)

In the formulae, $R^1$, $R^2$, $R^3$, $R^4$, Y, X and A are the same as defined above.

In the above reaction scheme, $R^1$, $R^2$, $R^3$, $R^4$, Y, and X are the same as defined hereinabove. A represents a lower alkyl group, and specific examples are the same as those given above with regard to Process (i).

Specific examples of the compound of general formula (VI) as a starting material in the above reaction scheme include N-(4,6-dimethylpyrimidin-2-yl) N'-(2-methoxysulfonylbenzenesulfonyl) S-methylisothiourea, N-(4,6-dimethylpyrimidin-2-yl) N'-(2-ethoxysulfonylbenzenesulfonyl) S-methylisothiourea, N-(4,6-dimethylpyrimidin-2-yl) N'-(2-morpholinosulfonylbenzenesulfonyl) S-methylisothiourea, N-(4,6-dimethylpyrimidin-2-yl) N'-(2-methylaminosulfonylbenzenesulfonyl) S-methylisothiourea, N-(4,6-dimethylpyrimidin-2-yl) N'-(2-aminosulfonylbenzenesulfonyl) S-methylisothiourea, and N-(4,6-dimethoxy-1,3,5-triazin-2-yl) N'-(2-methoxysulfonylbenzenesulfonyl) S-methylisothiourea.

Specific examples of the compound of the starting compound of general formula (VII) include O-methylhydroxylamine, O-ethylhydroxylamine, hydroxylamine, N-methoxy-2-ethoxysulfonylbenzenesulfonamide, and N,N-dimethylhydrazine.

An illustrative example of Process (iii) is as follows:

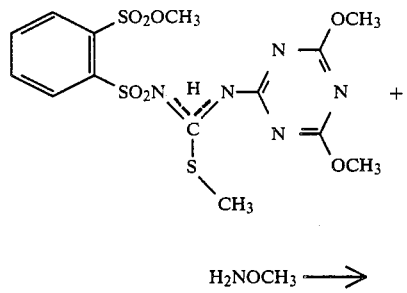

H$_2$NOCH$_3$ ⟶

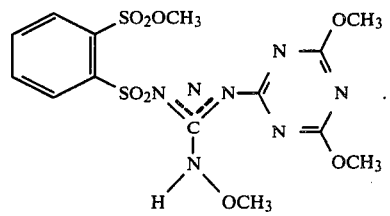

Desirably, the Process (iii) is carried out by using the same inert solvent or diluent as exemplified above, and the final desired product of high purity can be obtained in a high yield.

The above process, as is the case with the Processes (i) and (ii), can be carried out over a broad temperature range. Desirably, the reaction is carried out under normal atmospheric pressure, but it is also possible to operate under elevated or reduced pressures.

The compounds of this invention can be easily produced in accordance with the above Processes (i), (ii) and (iii). Among them, N,N'-bis-(2-substituted benzenesulfonyl)guanidine derivatives in which the group

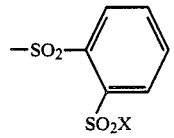

is substituted at each of the two nitrogen atoms of the guanidine skeleton can also be produced by the following alternative processes.

Alternative process (a)

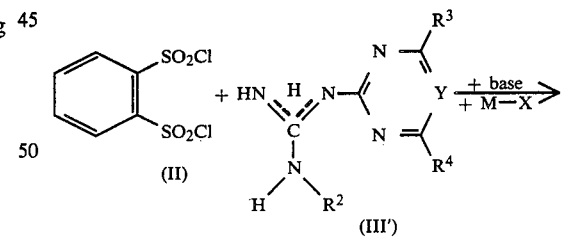

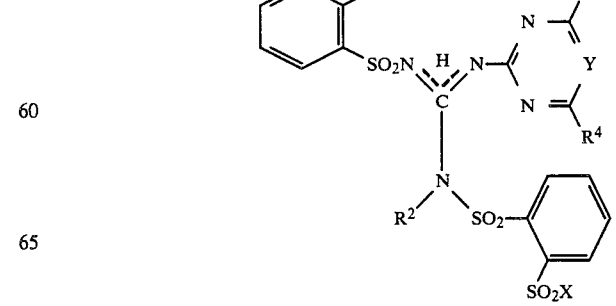

Alternative process (b)

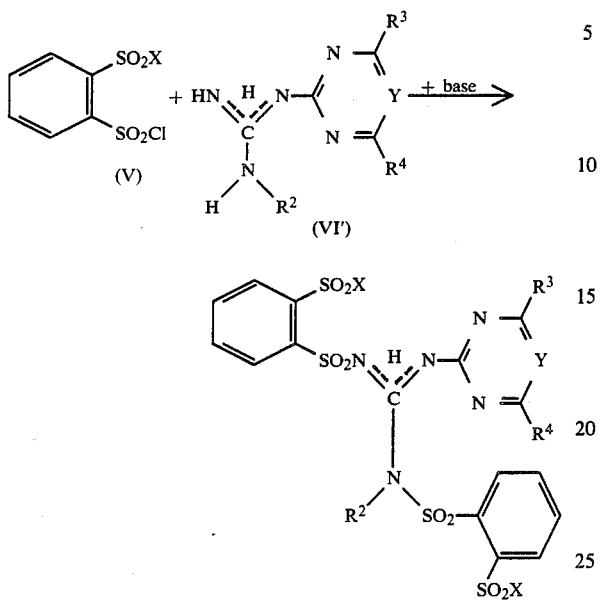

In the Alternative Processes (a) and (b), the desired compounds of this invention can be efficiently produced by reacting one mole of the starting compounds of general formula (II) and (V) with about 2 to about 2.5 moles of the other starting compounds (III') and (VI'), respectively.

Typical examples of the alternative processes are shown below.

Typical example (a)-1

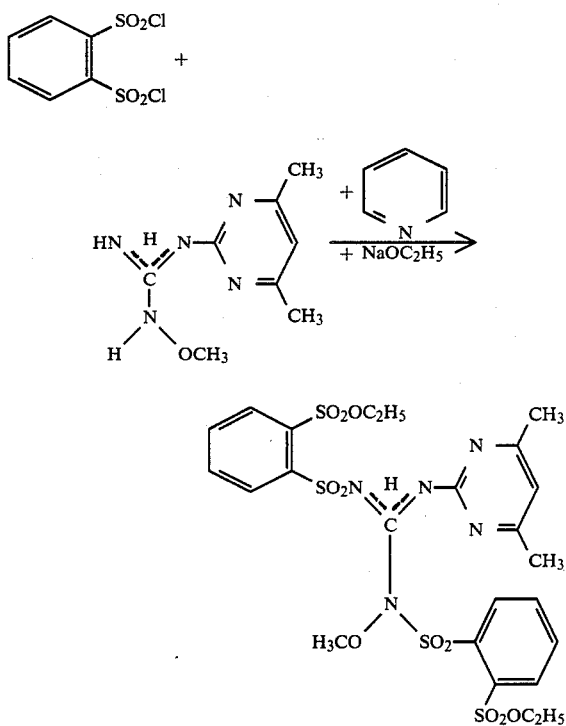

Typical example (b)-1

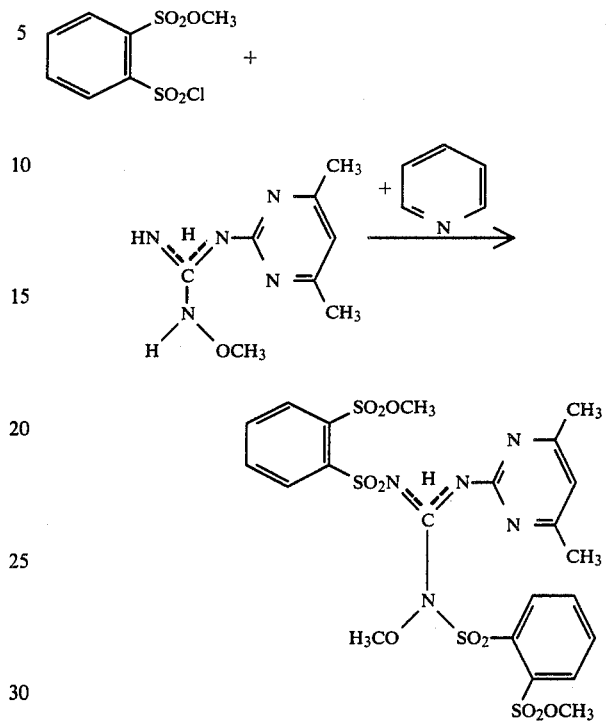

The above processes can be carried out by using the same inert solvent and diluent as exemplified hereinabove to given the final products in high purities and yields. The reaction conditions may be the same as those given above with regard to Process (i).

As a herbicide, the compounds of this invention represented by general formula (I) may be used directly upon dilution with water, or in various formulations obtained by methods generally practiced in the production of agricultural chemicals using agriculturally acceptable adjuvants. In actual use, these various formulations may be applied directly or after diluting them with water to the desired concentrations.

The agriculturally acceptable adjuvants as referred to herein include, for example, diluents (solvents, extenders, carriers), surface-active agents (soluilizing agents, emulsifiers, dispersing agents, wetting agents), stabilizers, stickers, aerosol propellants and synergists.

Examples of the solvents are water, and organic solvents, for example hydrocarbons [such as n-hexane, petroleum ether, petroleum fractions (e.g., paraffin waxes, kerosene, light oils, middle oils and heavy oils), benzene, toluene, and xylene], halogenated hydrocarbons (such as methylene chloride, carbon tetrachloride, ethylene chloride, ethylene dibromide, chlorobenzene and chloroform), alcohols (such as methanol, ethanol, propanol and ethylene glycol) ethers (such as diethyl ether, ethylene oxide and dioxane), alcohol ethers (such as ethylene glycol monomethyl ether), ketones (such as acetone and isophorone), esters (such as ethyl acetate and amyl acetate), amides (such as dimethylformamide and dimethylacetamide) and sulfoxides (such as dimethyl sulfoxide).

Examples of the extenders or carriers include inorganic powders, for example slaked lime, magnesium lime, gypsum, calcium carbonate, silica, perlite, pumice, calcite, diatomaceous earth, amorphous silica, alumina, zeolites, and clay minerals (such as pyrophyllite, talc, montmorillonite, beidellite, vermiculite, kaolinite and mica); vegetable powders such as cereal powders, starches, processed starches, sugar, glucose and crushed stalks of plants, and powders of synthetic resins such as phenolic resins, urea resins, and vinyl chloride resins.

Examples of the surface-active agents include anionic surface-active agents such as alkylsulfonic acid esters (such as sodium laurylsulfate), arylsulfonic acids (such as alkylarylsulfonic acid salts and sodium alkylnaphthalenesulfonates), succinic acid salts, and salts of sulfuric acid esters of polyethylene glycol alkylaryl ethers; cationic surface-active agents such as alkylamines (e.g., laurylamine, stearyl trimethyl ammonium chloride and alkyl dimethylbenzyl ammonium chloride) and polyoxyethylene alkylamines; nonionic surface-active agents such as polyoxyethylene glycol ethers (e.g., polyoxyethylene alkylaryl ethers and the condensation products thereof), polyoxyethylene glycol esters (e.g., polyoxyethylene fatty acid esters), and polyhydric alcohol esters (e.g., polyoxyethylene sorbitan monolaurate); and amphoteric surface-active agents.

Examples of other adjuvants include stabilizers; stickers (such as agricultural soaps, casein lime, sodium alginate, polyvinyl alcohol, vinyl acetate-type adhesives and acrylic adhesives); effect-prolonging agents; dispersion stabilizers [such as casein, tragacanth, carboxymethyl cellulose (CMC), and polyvinyl alcohol (PVA)]; and synergists.

The compounds of this invention can be formulated into various forms by methods generally practiced in the production of agricultural chemicals. Illustrative of such forms are emulsifiable concentrates, oil preparations, wettable powders, soluble powders, suspensions, dusts, granules, and pulverulent preparations.

The herbicide of this invention may contain about 0.001 to about 100% by weight, preferably about 0.005 to about 95% by weight, of the aforesaid active ingredient.

In actua use, the suitable amount of the active compound in the aforesaid various formulations and ready-to-use preparations is generally about 0.01 to about 95% by weight, preferably about 0.05 to about 60% by weight. The content of the active ingredient can be properly varied depending upon the type of the formulation, the method, purpose, time and locus of its application, and the state of occurrence of weeds.

If required, the compounds of this invention represented by general formula (I) may be used in combination with other agricultural chemicals, for example insecticides, fungicides, miticides, nematocides, antiviral agents, other herbicides, plant growth regulators and attractants [such as organophosphate compounds, carbamate compounds, dithio (or thiol) carbamate compounds, organochlorine compounds, dinitro compounds, organosulfur or organometallic compounds, antibiotics, substituted diphenyl ether compounds, urea compounds, and triazine compounds], and/or fertilizers.

Various formulations and ready-to-use preparations containing the aforesaid active ingredient of the invention can be applied by various methods generally practiced in the field of agricultural chemical application, for example spraying (liquid spraying, misting, atomizing, dusting, granule scattering, water surface application, pouring, etc.); and soil application (mixing, sprinkling, etc.). It can also be used by the so-called ultralow volume spraying method. According to this method, the active ingredient may be included in an amount of 100%.

The rate of application per unit area is, for example, about 0.01 to about 3 kg, preferably about 0.025 to about 1 kg, per hectare. In special cases, however, it may, and sometimes should, be outside the specified range.

According to this invention, there can be provided a herbicidal composition comprising the compound of general formula (I) as an active ingredient and a diluent (a solvent and/or an extender and/or a carrier) and/or a surface-active agent, and if further required, a stabilizer, a sticker, a synergist, etc.

This invention also provides a method for controlling weeds, which comprises applying to weeds and/or their habitat the compound of general formula (I) alone or in admixture with a diluent (a solvent and/or an extender and/or a carrier) and/or a surface-active agent and if further required, a stabilizer, a sticker, a synergist, etc.

The following examples illustrate the present invention more specifically. It should be understood however that the invention is in no way limited to these examples alone.

EXAMPLE 1

N-(4,6-Dimethylpyrimidin-2-yl) N'-methoxyguanidine (9.75 g) was dissolved in pyridine (200 ml), and 1,2-benzenedisulfonyl chloride (13.75 g) was added to the solution, and the mixture was stirred at room temperature for 2 days. After the reaction, pyridine was evaporated under reduced pressure.

The residual oil was extracted with methylene chloride.

The organic layer was washed with a 1N aqueous hydrochloric acid, and dried over sodium sulfate. Methylene chloride was evaporated under reduced pressure.

The residue was heated with sodium methylate (0.05 mol) in methanol at 50° C. for 2 hours.

The reaction mixture was poured into water and the aqueous alkaline solution was neutralized with hydrochloric acid, and the residue was collected by filtration.

Recrystallization of the residue from methanol gave 10 g of the desired N-(4,6-dimethylpyrimidin-2-yl) N'-(2-methoxysulfonylbenzenesulfonyl) N''-methoxyguanidine represented by the following formula. m.p. 130°–138° C.

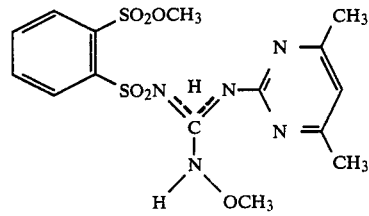

(Compound No. 1)

EXAMPLE 2

N-(4,6-Dimethylpyrimidin-2-yl) N'-methoxyguanidine (9.75 g) was a dissolved in pyridine (200 ml), and 2-methoxysulfonylbenzenesulfonyl chloride (13.5 g) was added to the solution. The mixture was stirred at room temperature for 2 days. The reaction mixture was poured into water, and extracted with methylene chloride. The organic layer was washed with a 1N aqueous solution of hydrochloric acid, and dried over anhydrous sodium sulfate. Methylene chloride was evaporated under reduced pressure, and the residue was recrystallized from methanol to give 10 g of the desired N-(4,6-dimethylpyrimidin-2-yl) N'-(2-methoxysulfonylbenzenesulfonyl) N''-methoxyguanidine represented by the following formula. mp. 130°–138° C.

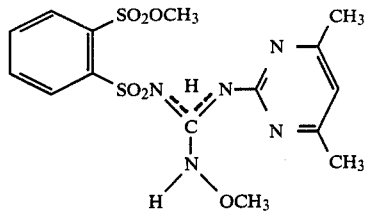

(Compound No. 1)

EXAMPLE 3

N-(4,6-Dimethoxy-1,3,5-triazin-2-yl) N'-(2-methoxysulfonylbenzenesulfonyl) S-methylisothiourea (4.63 g) was dissolved in dioxane (100 ml), and O-methylhydroxylamine (2.35 g) was added to the solution. The mixture was stirred at room temp. for 4 days. The reaction mixture was poured into ice water, and adjusted to pH 3 with hydrochloric acid. The precipitated crude crystals were collected by filtration, and recrystallized from acetonitrile to give 1.5 g of the desired N-(4,6-dimethoxy-1,3,5-triazin-2-yl) N'-(2-methoxysulfonylbenzenesulfonyl) N''-(methoxy)guanidine represented by the following formula. mp. 148°–150° C.

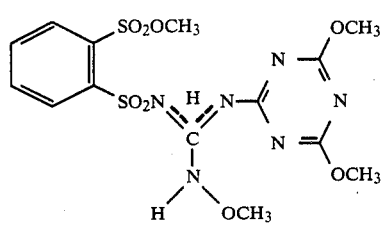

(Compound No. 12)

By the same method as in Example 1 or 2, the compounds of the invention shown in Table 1 below were synthesized.

TABLE 1

| Compound No. | X | $R^1$ | $R^2$ | $R^3$ | $R^4$ | Y | Physical constant |
|---|---|---|---|---|---|---|---|
| 2 | —OC$_2$H$_5$ | H | —OCH$_3$ | —CH$_3$ | —CH$_3$ | CH | mp. 168–171° C. |
| 3 | —N(morpholino) | H | —OCH$_3$ | —CH$_3$ | —CH$_3$ | CH | mp. 179–181° C. |
| 4 | —NHCH$_3$ | H | —OCH$_3$ | —CH$_3$ | —CH$_3$ | CH | mp. 218–219° C. |

EXAMPLE 4

Table 2 below shows compounds of this invention synthesized in accordance with the method of Example 1 or 2 using the indicated starting materials.

TABLE 2

| Compound No. | Starting material | | Compound of the invention |
|---|---|---|---|
| 5 | (structure with SO$_2$Cl, SO$_2$Cl) + HN=C(NHOCH$_3$)-N=pyrimidine(CH$_3$)$_2$ | , NH$_3$, | (structure with SO$_2$NH$_2$, SO$_2$N=C) |
|  | and pyridine as a base (equimolar reaction) | | |
| 6 | (structure with SO$_2$OCH$_3$, SO$_2$Cl) + HN=C(NHOCH$_3$)-N=pyrimidine(CH$_3$,OCH$_3$) | | (structure with SO$_2$OCH$_3$, SO$_2$N=C) |
|  | and pyridine as a base (equimolar reaction) | | |

EXAMPLE 5

Table 3 shows compounds of this invention synthesized in accordance with the Alternative Process (a) or (b) using the indicated starting materials.

TABLE 3

| Compound No. | Starting material | Compound of the invention |
|---|---|---|
| 7 | 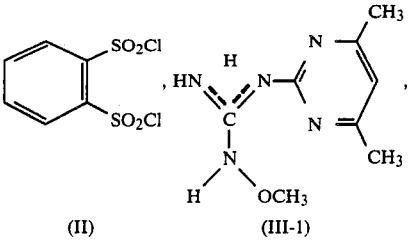 (II) + (III-1), NaOC₂H₅, (IV-1) and pyridine as a base [Reaction mole ratio] (II):(III-1):(IV-1) = 2.2:1:2.2 | 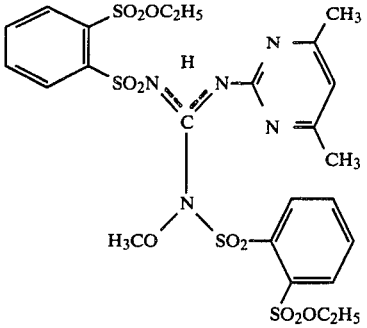 |
| 8 | 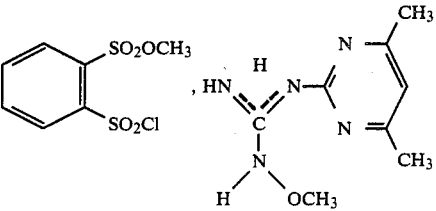 (V-1) + (III-1) and pyridine as a base [Reaction mole ratio] (V-1):(III-1) = 2.3:1 | 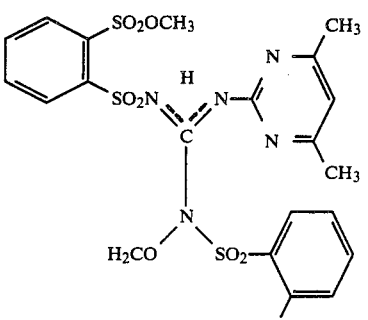 |

EXAMPLE 6

The compounds of this invention may be present in the form of alkali metal salts. Specific examples of such compounds synthesized are shown in Table 4.

TABLE 4

| Compound No. | Compound of the invention |
|---|---|
| 9 | 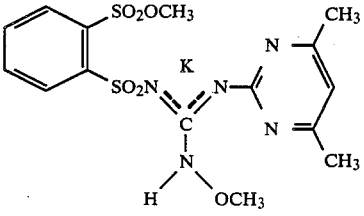 |
| 10 | 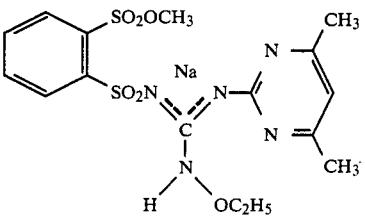 |
| 11 | 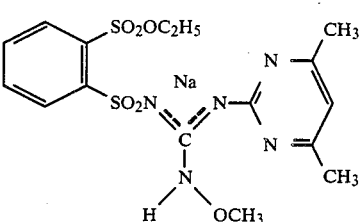 |

EXAMPLE 7

(Wettable Powder)

Fifteen parts of compound No. 1 of the invention, 80 parts of a 1:5 mixture of powdery diatomaceous earth and powdery clay, 2 parts of sodium alkylbenzenesulfonate, and 3 parts of a sodium alkylnaphthalenesulfonate/formaldehyde condensate are pulverized and mixed to form a wettable powder. It is diluted with water and dropped onto weeds and/or their habitat.

EXAMPLE 8

(Emulsifiable Concentrate)

Thirty parts of compound No. 2 of the invention, 55 parts of xylene, 8 parts of polyoxyethylene alkyl phenyl ether and 7 parts of calcium alkylbenzenesulfonate are mixed with stirring to form an emulsifiable concentrate. It is diluted with water and dropped onto weeds and/or their habitat.

EXAMPLE 9

(Dust)

Two parts of compound No. 3 of the invention and 98 parts of powdery clay are pulverized and mixed to form a dust. It is scattered over weeds and/or their habitat.

EXAMPLE 10

(Dust)

Compound No. 4 of the invention (1.5 parts), 0.5 parts of isopropyl hydrogen phosphate (PAP) and 98 parts of powdery clay are mixed while pulverizing them to form a dust. It is scattered over weeds and/or their habitat.

EXAMPLE 11

(Granules)

Water (25 parts) is added to a mixture consisting of 10 parts of compound No. 1 of the invention, 30 parts of bentonite (montmorillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered over weeds and/or their habitat.

EXAMPLE 12

(Granules)

Ninety-five parts of clay mineral particles having a particle size distribution between 0.2 and 2 mm are put in a rotary mixer, and with rotation, 5 parts of compound No. 2 of the invention is sprayed onto the particles to wet them uniformly and the particles are dried to form granules. The granules are scattered over weeds and/or their habitat.

EXAMPLE 13

(Biological Test)

Test of foliar/soil treatment of upland farm weeds and crops after emergence:

Preparation containing active compound

Carrier: 5 parts by weight of acetone
Emulsifier: 1 part by weight of benzyloxypolyglycol ether A preparation containing the active compound is formed by mixing 1 part by weight of each of the active compounds with the carrier and emulsifier in the amounts indicated above, and diluting a predetermined amount of the resulting emulsifiable concentrate with water.

Testing procedure

Seeds of wheat were sown in 1000 cm$^2$ pots filled with upland farm soil, and soil containing seeds of each of *Alopecurus aequalis* Sobol. var. amurensis Ohwi, *Stellaria media* Villars., and *Stellaria alsine* Grimn was applied to the soil to cover it to a depth of 1 cm.

Ten days after germination (when the wheat and the weeds were in the two-leaf stage), 10 ml of the chemical in a concentration of 25 ppm was sprayed uniformly onto the surface layer of the soil in each of the test pots.

Four weeks after spraying, the herbicidal effect and the degree of phytotoxicity to wheat were examined by the following standards.

Evaluation of the herbicidal effect (herbicidal rate based on the non-treated area):
5: at least 95% (withered)
4: at least 80% but less than 95%
3: at least 50% but less than 80%
2: at least 30% but less than 50%
1: at least 10% but less than 30%
0: less than 10% (no effect)

Evaluation of phytotoxicity to wheat (the phytotoxicity rate based on the non-treated area):
5: at least 90% (fatal injury)
4: at least 50% but less than 90%
3: at least 30% but less than 50%
2: at least 10% but less than 30%
1: more than 0% but less than 10%
0: 0% (no phytotoxicity)

The results are shown in Table 5.

TABLE 5

| Compound No. | Amount of the active ingredient (kg/ha) | Herbicidal effect | | | Phytotoxicity to wheat |
|---|---|---|---|---|---|
| | | A. aequalis | S. media | S. alsine | |
| 1 | 0.025 | 5 | 5 | 5 | 0 |
| 2 | 0.025 | 5 | 5 | 5 | 0 |
| 3 | 0.025 | 5 | 5 | 5 | 0 |
| 6 | 0.025 | 5 | 5 | 5 | 0 |
| 7 | 0.025 | 5 | 5 | 5 | 0 |
| Simazine (control) | 0.4 | 3 | 5 | 5 | 1 |

Note
1. Simazine (control; commercial paroduct): 2-Chloro-4,6-bis(ethylamino)-1,3,5-triazine (50% wettable powder).

EXAMPLE 14

(Biological Test)

Test of pre-emergence soil treatment of upland farm weeds and crops:

Testing procedure

Soybean seeds were sown in 1000 cm$^2$ pots filled with upland farm soil, and soil containing seeds of each of *Digitaria adscendens* Henr., *Amaranthus lividus* Loisel., *Chenopodium album* L., and *Echinochloa crus-galli* P. Beauv. was applied to the soil to cover it to a depth of 1 cm. One day after sowing and soil covering, 10 ml of a chemical having a concentration of 100 ppm and prepared in the same way as in Example 13 was sprayed uniformly onto the surface layer of the soil in each test pot.

Four weeks after spraying, the herbicidal effect and the degree of phytotoxicity to soybean were examined by the same standards as in Example 13.

The results are shown in Table 6.

TABLE 6

| Compound No. | Amount of the active ingredient (kg/ha) | Herbicidal effect | | | | Phytotoxicity to soybean |
|---|---|---|---|---|---|---|
| | | D. adscendens | E. crus-galli | C. album | A. lividus | |
| 1 | 0.1 | 5 | 5 | 5 | 5 | 0 |
| 2 | 0.1 | 5 | 5 | 5 | 5 | 0 |
| Simazine (control) | 0.4 | 3 | 3 | 5 | 5 | 1 |

Note
1. Simazine (control) is the same as the footnote to Table 5.

It will be understood that the specification and examples are illustrative but not limitative of the present invention and that other embodiments within the spirit and scope of the invention will suggest themselves to those skilled in the art.

What is claimed is:

1. A sulfonylguanidine derivative of the formula

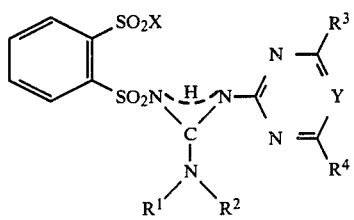

in which
R¹ is a hydrogen atom or the group

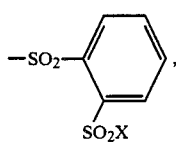

R² is a hydroxy group, a lower alkoxy group or a di-lower alkylamino group,
R³ and R⁴ each independently is a lower alkyl group or a lower alkoxy group,
X is a lower alkoxy group, a lower alkylamino group or a morpholino group, and
Y is CH.

2. A compound according to claim 1, wherein such compound is N-(4,6-dimethylpyrimidin-2-yl) N'-(2-methoxysulfonylbenzenesulfonyl) N''-methoxyguanidine of the formula

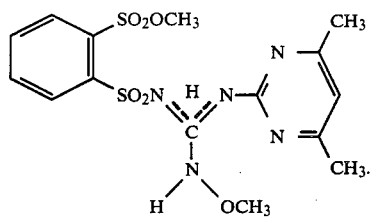

3. A compound according to claim 1, wherein such compound is N-(4,6-dimethylpyrimidin-2-yl) N'-(2-ethoxysulfonylbenzenesulfonyl) N''-methoxyguanidine of the formula

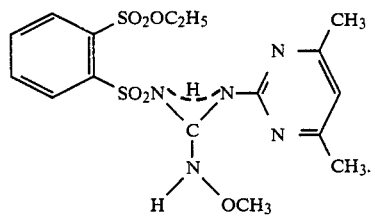

4. A compound according to claim 1, wherein such compound is N-(4,6-dimethylpyrimidin-2-yl) N'-morpholinosulfonylbenzenesulfonyl N''-methoxyguanidine of the formula

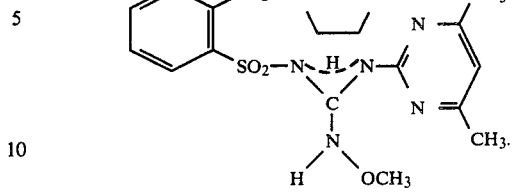

5. A compound according to claim 1, wherein such compound is N-(4-methoxy-6-methylpyrimidin-2-yl) N'-(2-methoxysulfonylbenzenesulfonyl) N''-methoxyguanidine of the formula

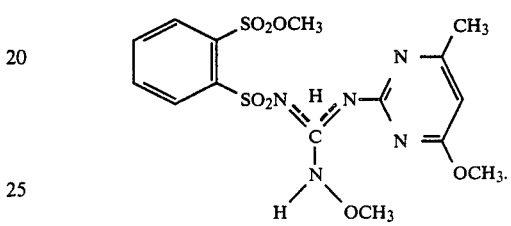

6. A compound according to claim 1, wherein such compound is N-(4,6-dimethylpyrimidin-2-yl) N',N''-bis-(2-ethoxysulfonylbenzenesulfonyl) N'-methoxyguanidine of the formula

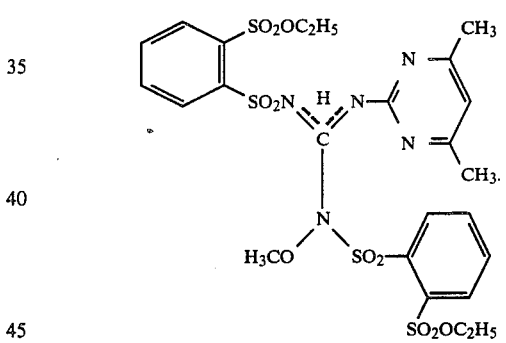

7. A herbicidal composition comprising a herbicidally effective amount of a compound according to claim 1 in admixture with a diluent.

8. A method of combating unwanted vegetation which comprises administering to such vegetation or to a location from which it is desired to exclude such vegetation a herbicidally effective amount of a compound according to claim 1.

9. The method according to claim 8, wherein such compound is
N-(4,6-dimethylpyrimidin-2-yl) N'-(2-methoxysulfonylbenzenesulfonyl) N''-methoxyguanidine,
N-(4,6-dimethylpyrimidin-2-yl) N'-(2-ethoxysulfonylbenzenesulfonyl) N''-methoxy-guanidine,
N-(4,6-dimethylpyrimidin-2-yl) N'-morpholinosulfonylbenzenesulfonyl N''-methoxyguanidine,
N-(4-methoxy-6-methylpyrimidin-2-yl) N'-(2-methoxysulfonylbenzenesulfonyl) N''-methoxyguanidine or
N-(4,6-dimethylpyrimidin-2-yl) N',N''-bis-(2-ethoxysulfonylbenzenesulfonyl) N'-methoxyguanidine.

* * * * *